US010034636B2

(12) United States Patent
Huang

(10) Patent No.: US 10,034,636 B2
(45) Date of Patent: *Jul. 31, 2018

(54) TRANSDERMAL MICRONEEDLE ARRAY PATCH AND METHOD FOR MANUFACTURING THE SAME

(71) Applicant: Micro Nipple Technology Co., Ltd., Taipei (TW)

(72) Inventor: Juang-Tang Huang, Taipei (TW)

(73) Assignee: Micro Nipple Technology Co., Ltd.

( * ) Notice: Subject to any disclaimer, the term of this patent is extended or adjusted under 35 U.S.C. 154(b) by 1054 days.

This patent is subject to a terminal disclaimer.

(21) Appl. No.: 14/269,080

(22) Filed: May 3, 2014

(65) Prior Publication Data
US 2015/0208985 A1    Jul. 30, 2015

(30) Foreign Application Priority Data
Jan. 28, 2014    (TW) .............................. 103103312 A

(51) Int. Cl.
| A61B 5/05 | (2006.01) |
| A61B 5/00 | (2006.01) |
| A61B 5/1473 | (2006.01) |
| B32B 37/24 | (2006.01) |
| A61B 5/145 | (2006.01) |
| A61B 5/15 | (2006.01) |

(52) U.S. Cl.
CPC ............ *A61B 5/685* (2013.01); *A61B 5/1473* (2013.01); *A61B 5/14532* (2013.01); *A61B 5/14546* (2013.01); *A61B 5/150022* (2013.01); *A61B 5/150282* (2013.01); *B32B 37/24* (2013.01); *A61B 5/14514* (2013.01); *A61B 5/150984* (2013.01); *A61B 5/6833* (2013.01); *A61B 2562/046* (2013.01); *A61B 2562/125* (2013.01); *B32B 2037/243* (2013.01); *B32B 2535/00* (2013.01); *Y10T 156/10* (2015.01)

(58) Field of Classification Search
CPC .... A61B 5/685; A61B 5/1473; A61B 5/14532
See application file for complete search history.

(56) References Cited

U.S. PATENT DOCUMENTS

| 7,344,499 B1 | 3/2008 | Prausnitz et al. |
| 2010/0305473 A1* | 12/2010 | Yuzhakov ......... A61M 37/0015 600/575 |

(Continued)

*Primary Examiner* — Christian Jang
(74) *Attorney, Agent, or Firm* — Parker Ibrahim & Berg LLP; Stephen D. LeBarron

(57) ABSTRACT

The invention relates to a transdermal microneedle array patch for measuring a concentration of a hypodermal target molecule. The transdermal microneedle array patch includes a substrate, a microneedle unit, a signal processing unit and a power supply unit. The microneedle unit at least comprises a first microneedle set used as a working electrode and a second microneedle set used as a reference electrode, the first and second microneedle sets arranging on the substrate. Each microneedle set comprises at least a microneedle. The first microneedle set comprises at least a sheet having a through hole on which a barbule forms at the edge. One of the sheet provides the through hole from which the barbules at the edge of the other sheets go through, and the barbules are disposed separately.

20 Claims, 10 Drawing Sheets

(56) References Cited

U.S. PATENT DOCUMENTS

2015/0208970 A1\* 7/2015 Huang .................. A61B 5/685
 600/345
2015/0208984 A1\* 7/2015 Huang .................. A61B 5/685
 600/393

\* cited by examiner

TRANSDERMAL MICRONEEDLE ARRAY PATCH AND METHOD FOR MANUFACTURING THE SAME

BACKGROUND OF THE INVENTION

Field of the Invention

The invention relates to a transdermal microneedle array patch, particularly a transdermal microneedle array patch which obtains physiologic data of a human body by measuring the concentration of hypodermal target molecules.

Description of the Related Art

Tissue fluid is mainly contained in subcutaneous tissue and includes amino acids, sugars, fatty acids, coenzymes, hormones, neurotransmitters, salts and waste products from the cells. Moreover, the tissue fluid is also the major communication channel for cell and blood. The concentrations of the various components in the tissue fluid are useful for determining user's physiological conditions.

The medicine will be slowly released over a long period in tissue fluid when the patient takes or injects the medicine. The concentration variation of medicine in the tissue fluid is continually monitored during development of medicine and clinical experiment. Therefore, the tissue fluid is commonly sampled to further examine or analyze in medical treatment of patient.

The commercially available physiological examination instruments generally withdraw tissue fluid by using a needle piercing through stratum corneum. However, the patient may feel painful for this kind of invasive sampling way. Moreover, the patient may be infected by microorganism originally present on epidermis and entering the patient body as the stratum corneum is pierced by a needle. Transdermal sensor with array-arranged microneedles pricking through skin is developed to withdraw tissue fluid in painless and minimally-invasive way.

The array-arranged microneedles of a transdermal sensor can be manufactured with standard semiconductor process such as photolithograph process and etching process. U.S. Pat. No. 7,344,499 discloses a process for manufacturing silicon microneedles. As can be seen from the second paragraph of the twelve column of this patent, firstly a silicon wafer with a first patterned photoresist layer is prepared. Next, a through hole is defined on the wafer by anisotropic etching. Afterward, a chromium layer is coated on the wafer and a second patterned photoresist layer is formed atop the through hole to function as circular etching mask. Next, the wafer is then etched to form outer tapered wall for the microneedles. However, the silicon-based microneedles are brittle and tend to break when the microneedles prick through user's skin.

Alternatively, hollow microneedles with resin barbules are proposed, where the barbules are drilled by laser processing. Firstly, sheet with barbules is formed by extruding polyimide or polyether ether ketone, and then the barbules are drilled by laser to form hollow microneedles. However, the microneedles have compact size such that the barbules may have ragged edge after extrusion. Moreover, it is difficult to form a hollow microneedle with off-axis through hole or central through hole having uniform inner diameter by laser processing.

SUMMARY OF THE INVENTION

One object of the present invention is to provide a transdermal microneedle array patch, where the transdermal microneedle array patch has microneedles made by punching or etching to have sufficient mechanical strength. The microneedle can be kept intact after the microneedle pricks user's skin for sensing. The microneedle has such structure that the sensing polymer can be advantageously coated on inner surface of the tip of the microneedle. The sensing polymer can be prevented from falling as the microneedle pricks user's skin for sensing.

Accordingly, the present invention provides a transdermal microneedle array patch. The transdermal microneedle array patch includes a substrate, a microneedle unit, a signal processing unit and a power supply unit. The microneedle unit at least comprises a first microneedle set used as a working electrode and a second microneedle set used as a reference electrode, the first and second microneedle sets arranging on the substrate. Each microneedle set comprises at least a microneedle. The first microneedle set comprises at least a sheet having a through hole on which a barbule forms at the peripheral. One of the sheets provides the through hole from which the barbules at the edge of the other sheets go through, and the barbules are disposed separately.

The microneedles of the working electrode of the transdermal microneedle array patch according to the invention may be subjected to surface modification, in view of the target molecule to be sensed. The target molecule may be a biological molecule, such as glucose, cortisol or fatty acids. Also, the target molecule may be a pharmaceutical molecule, such as antibiotics. The transdermal microneedle array patch of the present invention may be used for pharmaceutical monitoring during the administration of a medication for a chronic disease or a specific pharmaceutical. Personalized medication of a specific dosage or frequency of administration can be provided based on the individual metabolism of the pharmaceutical.

The microneedle of the present invention has sufficient mechanical strength. The microneedle can be kept intact after the microneedle pricks user skin for sensing. Moreover, the microneedle has simple manufacture process, which is beneficial for mass production.

DETAILED DESCRIPTION OF THE INVENTION

Figure 1:
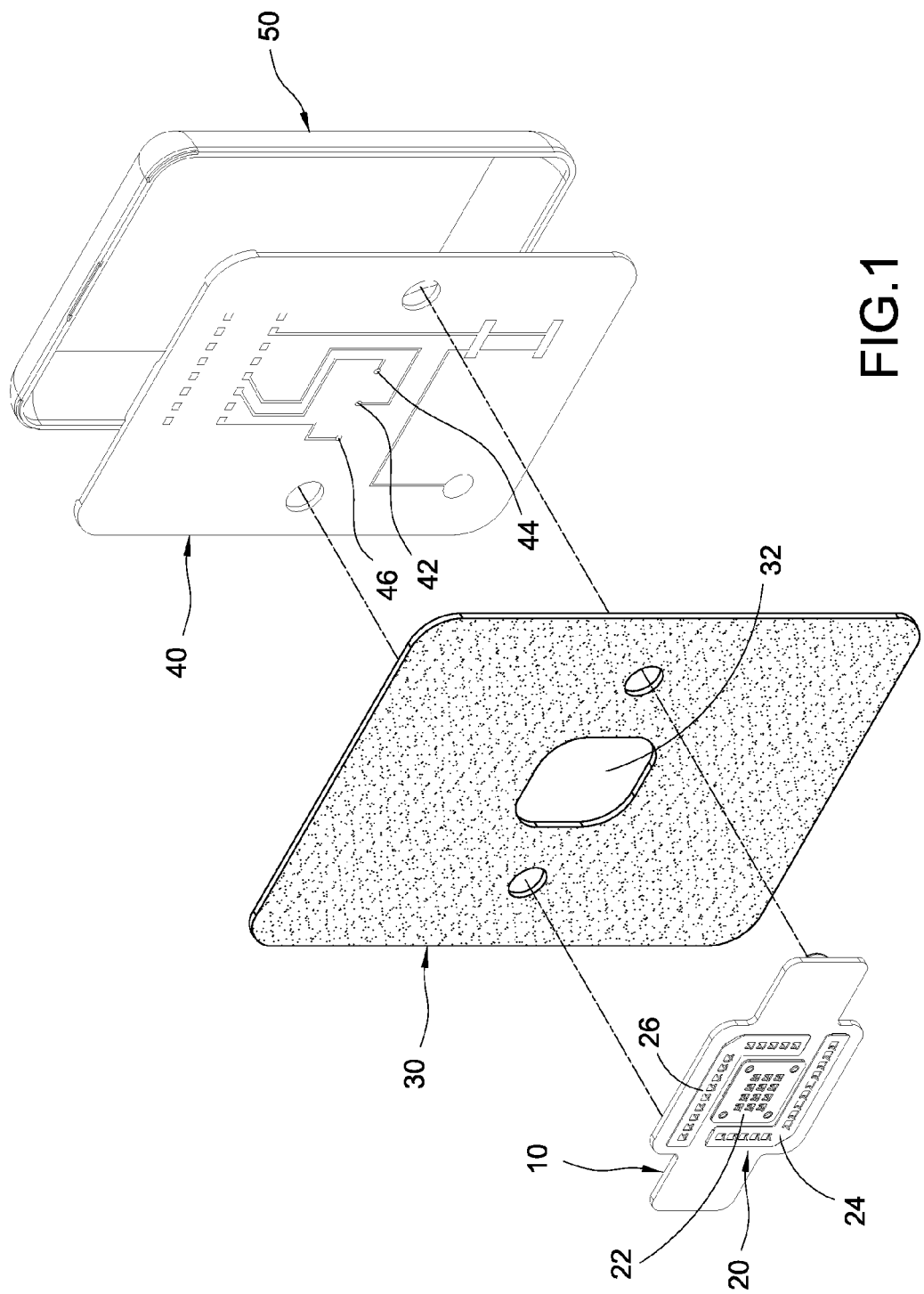
FIG. 1 shows the exploded view of the transdermal microneedle array patch according to an embodiment of the present invention from one viewing direction.
Figure 2:
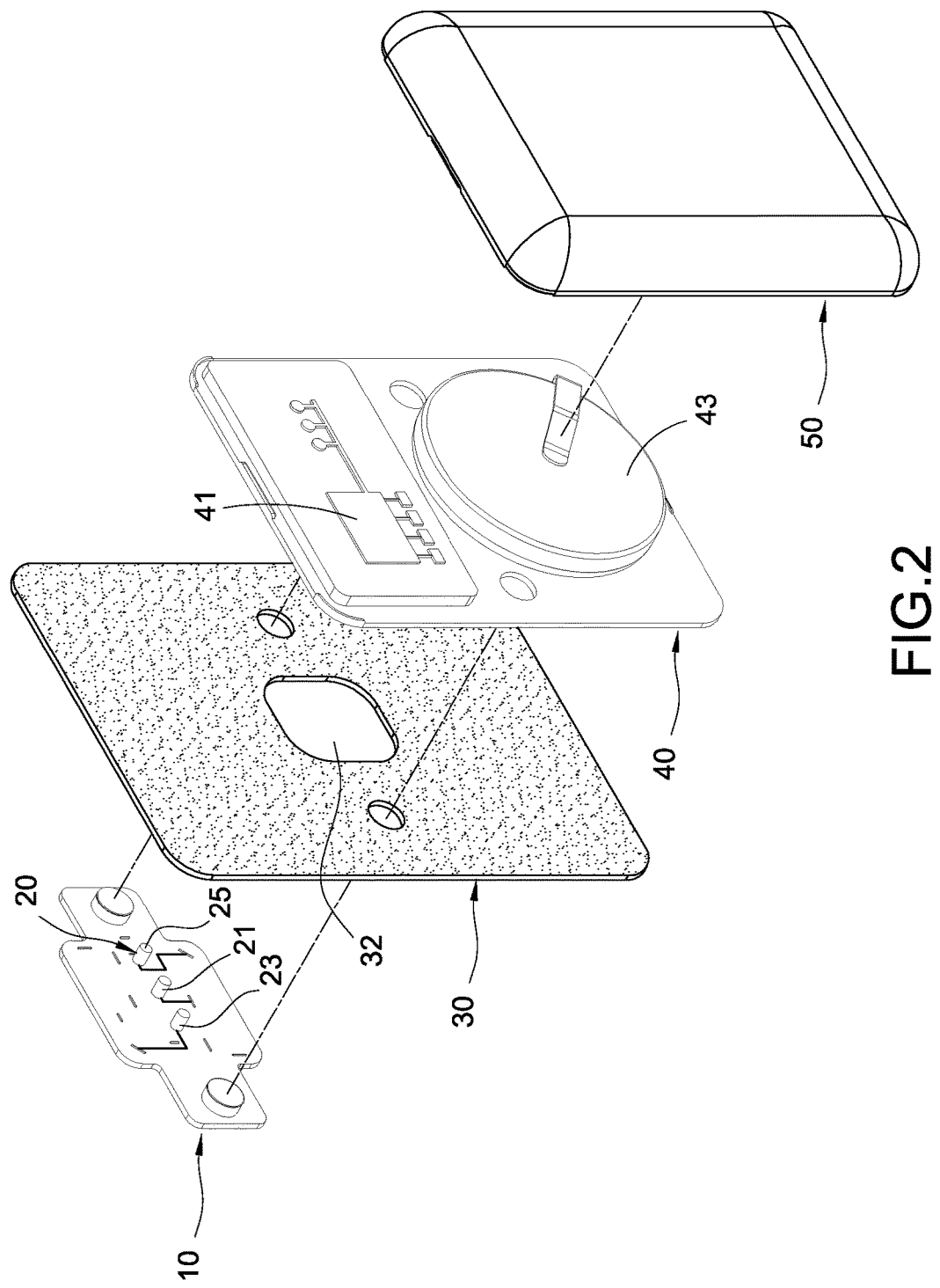
FIG. 2 shows the exploded view of the transdermal microneedle array patch from another viewing direction.

The features of the invention believed to be novel are set forth with particularity in the appended claims. The invention itself, however, may be best understood by reference to the following detailed description of the invention, which describes an exemplary embodiment of the invention, taken in conjunction with the accompanying drawings, in which:

FIG. 1 shows the exploded view of the transdermal microneedle array patch according to an embodiment of the present invention from one viewing direction, and FIG. 2 shows the exploded view of the transdermal microneedle array patch from another viewing direction. The transdermal microneedle array patch of the present invention mainly comprises a substrate 10, a microneedle unit 20, a flexible pad 30, a signal processing unit 41, a power supply unit 43 and a cover 50, where the signal processing unit 41 and the power supply unit 43 are arranged on a circuit board 40.

According to an embodiment of the present invention, the microneedle unit 20 comprises a first microneedle set 22 used as a working electrode, a second microneedle set 24 used as a reference electrode, and a third microneedle set 26 used as a counter electrode. The flexible pad 30 has an opening 32 through which the microneedle unit 20 passes. The microneedle unit 20 further comprises electric conducting posts 21, 23, 25 to respectively and electrically connect to the contacts 42, 44 and 46 on the circuit board 40. The transdermal microneedle array patch of the present invention uses the flexible pad 30 to have tight fit with the user's muscle during operating thereof.

The signal processing unit 41 electrically connects to the microneedle unit 20 and receives a concentration data of hypodermal target molecules sensed by the microneedle unit 20. The signal processing unit 41 generates a sensing signal manifesting the current physiological condition of user after processing the received concentration data. The power supply unit 43 provides working power to the transdermal microneedle array patch of the present invention.

Figure 3:
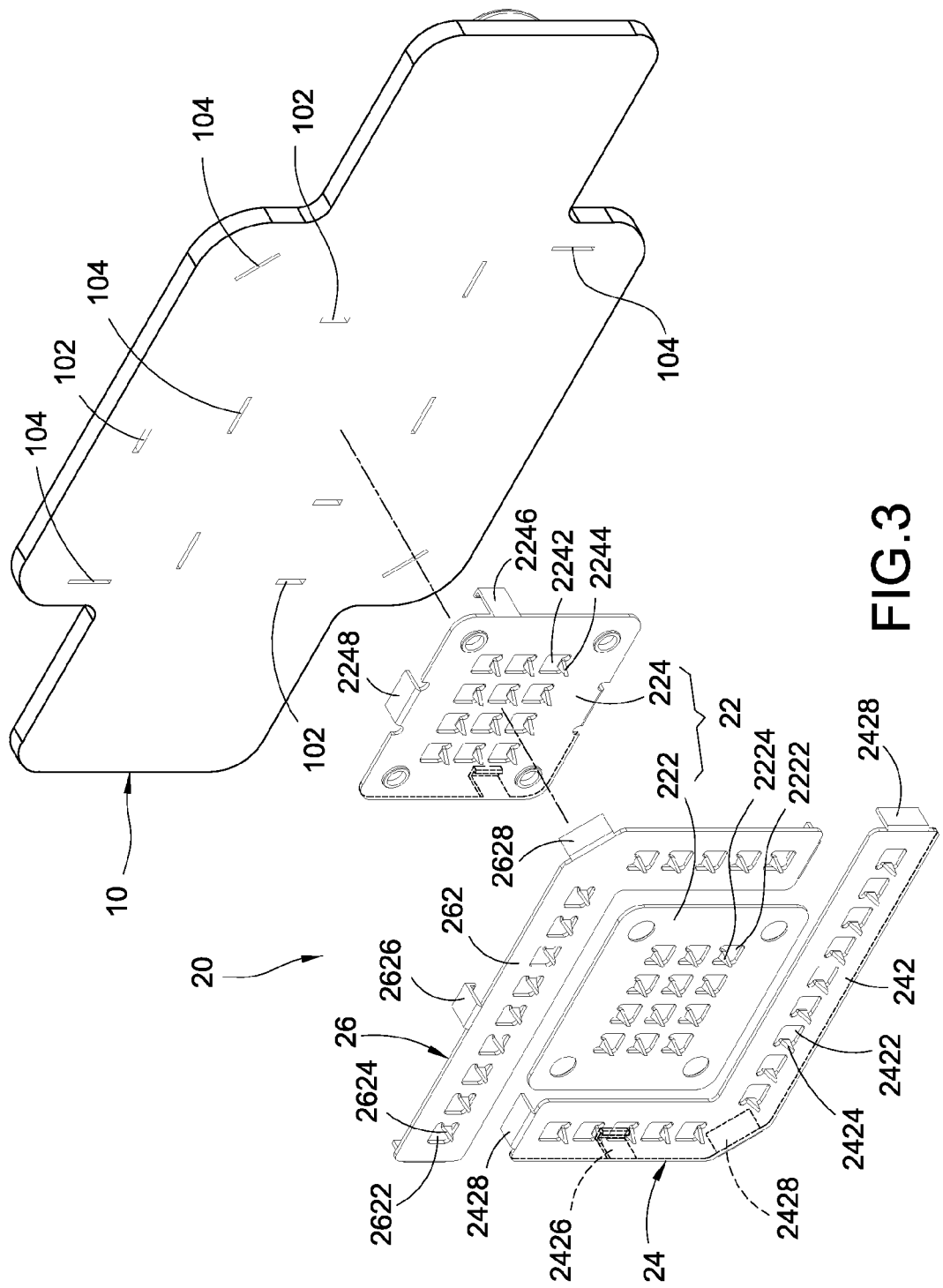
FIG. 3 shows a schematic exploded view of the microneedle unit according to an embodiment of the present invention.

FIG. 3 shows a schematic exploded view of the microneedle unit 20 according to an embodiment of the present invention. The first microneedle set 22 comprises a first sheet 222 and a second sheet 224 stacked with the first sheet 222. The first sheet 222 has at least one first through hole 2222 defined thereon, and a first barbule 2224 at peripheral of the first through hole 2222. The second sheet 224 has at least one second through hole 2242 defined thereon, and a second barbule 2244 at peripheral of the second through hole 2242, where the second barbule 2244 penetrates the first through hole 2222 to juxtapose the first barbule 2224. The second sheet 224 of the first microneedle set 22 comprises barb 2246 at the peripheral thereof and matched with the aperture 102 defined on the substrate 10. According to another embodiment, the second sheet 224 of the first microneedle set 22 comprises conductive pin 2248 at the peripheral thereof. The conductive pin 2248 can be inserted into a slot 104 defined on the substrate 10 to electrically connect to the conductive post 21.

Similarly, the second microneedle set 24 comprises a first sheet 242. The first sheet 242 has at least one first through hole 2422 defined thereon, and a first barbule 2424 at peripheral of the first through hole 2422. The first sheet 242 of the second microneedle set 24 comprises barb 2426 at the peripheral thereof and matched with the aperture 102 defined on the substrate 10. According to another embodiment, the first sheet 242 of the second microneedle set 24 comprises conductive pin 2428 at the peripheral thereof. The conductive pin 2428 can be inserted into a slot 104 defined on the substrate 10 to electrically connect to the conductive post 23.

Similarly, the third microneedle set 26 also comprises a first sheet 262. The first sheet 262 has at least one first through hole 2622 defined thereon, and a first barbule 2624 at peripheral of the first through hole 2622. The first sheet 262 of the third microneedle set 26 comprises barb 2626 at the peripheral thereof and matched with the aperture 102 defined on the substrate 10. According to another embodiment, the first sheet 262 of the third microneedle set 26 comprises conductive pin 2628 at the peripheral thereof. The conductive pin 2628 can be inserted into a slot 104 defined on the substrate 10 to electrically connect to the conductive post 25.

According to an embodiment of the present invention, the first microneedle set 22, the second microneedle set 24, and the third microneedle set 26 can be made by punching or etching process. The material of the barbules is selected from the group consisting of stainless steel, nickel, nickel alloy, titanium, titanium alloy, carbon nanotube, and silicon. The surface of the barbules is coated with biologically compatible metal. The material of the barbules can also be selected from the group consisting of polycarbonate, polymethacrylic acid, polytetrafluoroethylene, and polyester. The surface of the barbules is also coated with biologically compatible metal. Moreover, the height of the barbules is 300-600 micrometers; the base width of the barbules is 150-450 micrometers. The separation between tips of the barbules is 500-3000 micrometers.

With reference to FIGS. 4 to 7, FIG. 4 is a top view of the microneedle set functioning as working electrode according to an embodiment of the present invention. The first microneedle set 22 comprises a first sheet 222 and a second sheet 224 stacked with the first sheet 222. The first sheet 222 has at least one first through hole 2222 defined thereon, and a first barbule 2224 at peripheral of the first through hole 2222. The second sheet 224 has at least one second through hole 2242 defined thereon, and a second barbule 2244 at peripheral of the second through hole 2242, where the second barbule 2244 penetrates the first through hole 2222 to juxtapose the first barbule 2224.

Figure 5:
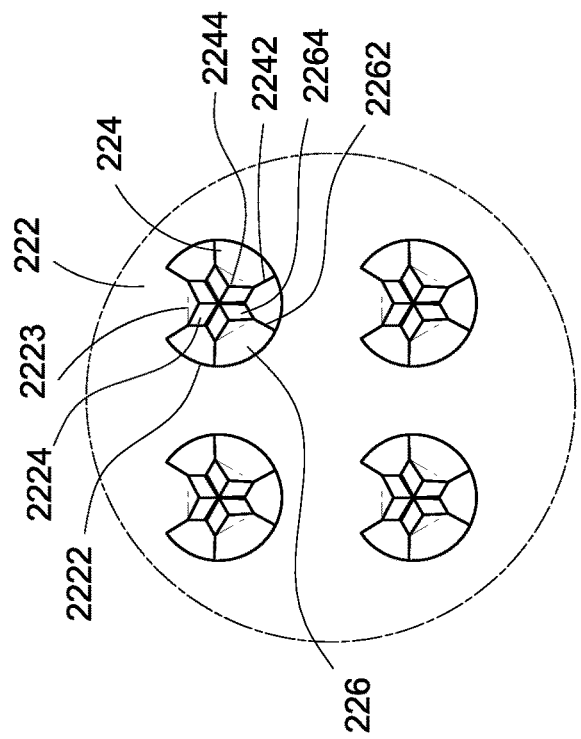
FIG. 5 is a top view of the microneedle set functioning as working electrode according to another embodiment of the present invention.
Figure 4:
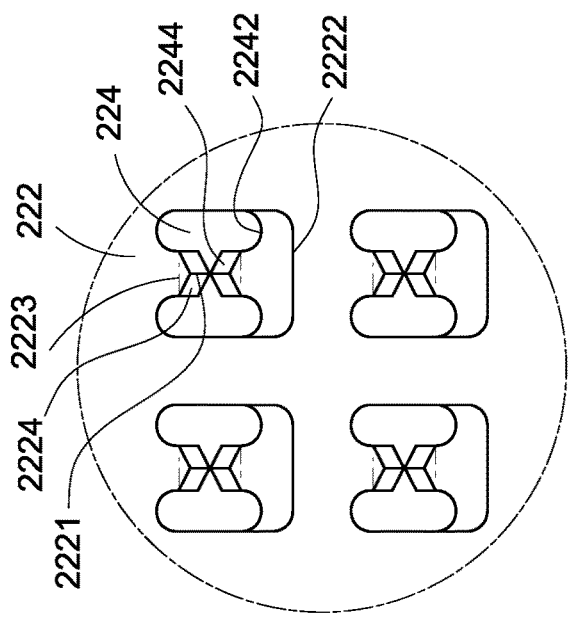
FIG. 4 is a top view of the microneedle set functioning as working electrode according to an embodiment of the present invention.

FIG. 5 is a top view of the microneedle set functioning as working electrode according to another embodiment of the present invention. The first microneedle set 22 comprises a first sheet 222, a second sheet 224 and a third sheet 226 stacked with each other. The first sheet 222 has at least one first through hole 2222 defined thereon, and a first barbule 2224 at peripheral of the first through hole 2222. The second sheet 224 has at least one second through hole 2242 defined thereon, and a second barbule 2244 at peripheral of the second through hole 2242. The third sheet 226 has at least one third through hole 2262 defined thereon, and a third barbule 2264 at peripheral of the third through hole 2262. The second barbule 2244 and the third barbule 2264 penetrates the first through hole 2222 to juxtapose the first barbule 2224, and the tips of the barbules are in right triangular arrangement from top view.

Figure 6:
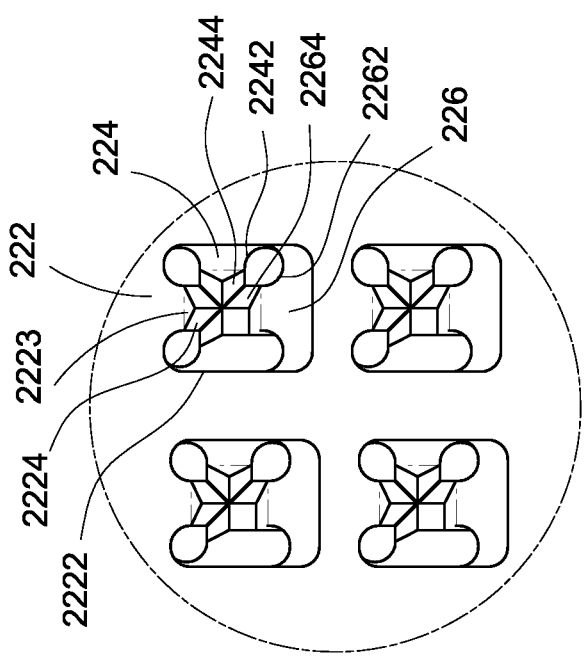
FIG. 6 is a top view of the microneedle set functioning as working electrode according to still another embodiment of the present invention.

FIG. 6 is a top view of the microneedle set functioning as working electrode according to still another embodiment of the present invention. The first microneedle set 22 comprises a first sheet 222, a second sheet 224 and a third sheet 226 stacked with each other. The first sheet 222 has at least one first through hole 2222 defined thereon, and a first barbule 2224 at peripheral of the first through hole 2222. The second sheet 224 has at least one second through hole 2242 defined thereon, and a second barbule 2244 at peripheral of the second through hole 2242. The third sheet 226 has at least one third through hole 2262 defined thereon, and a third barbule 2264 at peripheral of the third through hole 2262. The second barbule 2244 and the third barbule 2264 penetrates the first through hole 2222 to juxtapose the first barbule 2224, and the tips of the barbules are in isosceles triangular arrangement from top view.

Figure 7:
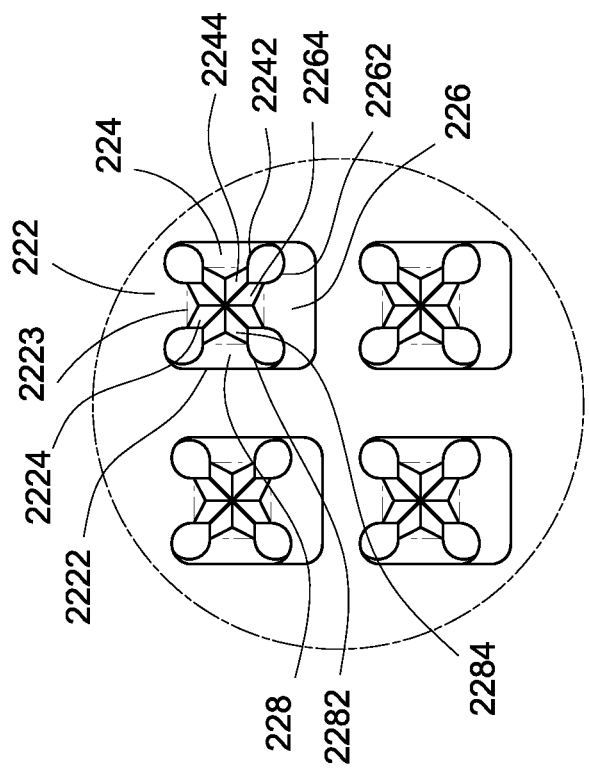
FIG. 7 is a top view of the microneedle set functioning as working electrode according to still another embodiment of the present invention.

FIG. 7 is a top view of the microneedle set functioning as working electrode according to still another embodiment of the present invention. The first microneedle set 22 comprises a first sheet 222, a second sheet 224, a third sheet 226 and a fourth sheet 228 stacked with each other. The first sheet 222 has at least one first through hole 2222 defined thereon, and a first barbule 2224 at peripheral of the first through hole 2222. The second sheet 224 has at least one second through hole 2242 defined thereon, and a second barbule 2244 at peripheral of the second through hole 2242. The third sheet 226 has at least one third through hole 2262 defined thereon, and a third barbule 2264 at peripheral of the third through hole 2262. The fourth sheet 228 has at least one fourth through hole 2282 defined thereon, and a fourth barbule 2284 at peripheral of the fourth through hole 2282. The second barbule 2244, the third barbule 2264 and the fourth barbule 228 penetrates the first through hole 2222 to juxtapose the first barbule 2224, and the tips of the barbules are in rectangular arrangement from top view.

In the embodiments shown in FIGS. 4 to 7, the barbule 2224 of the first microneedle set 22 comprises a tip 2221 and a base 2223. The tips of those barbules, after the sheets are stacked together, are not at the same altitudes. Namely, some barbules pass more through holes than other barbules. Alternatively, the height of the barbules can be such designed, based on the stacked order of sheets, that the tips of those barbules, after the sheets are stacked together, are at the same altitudes.

Figure 8:
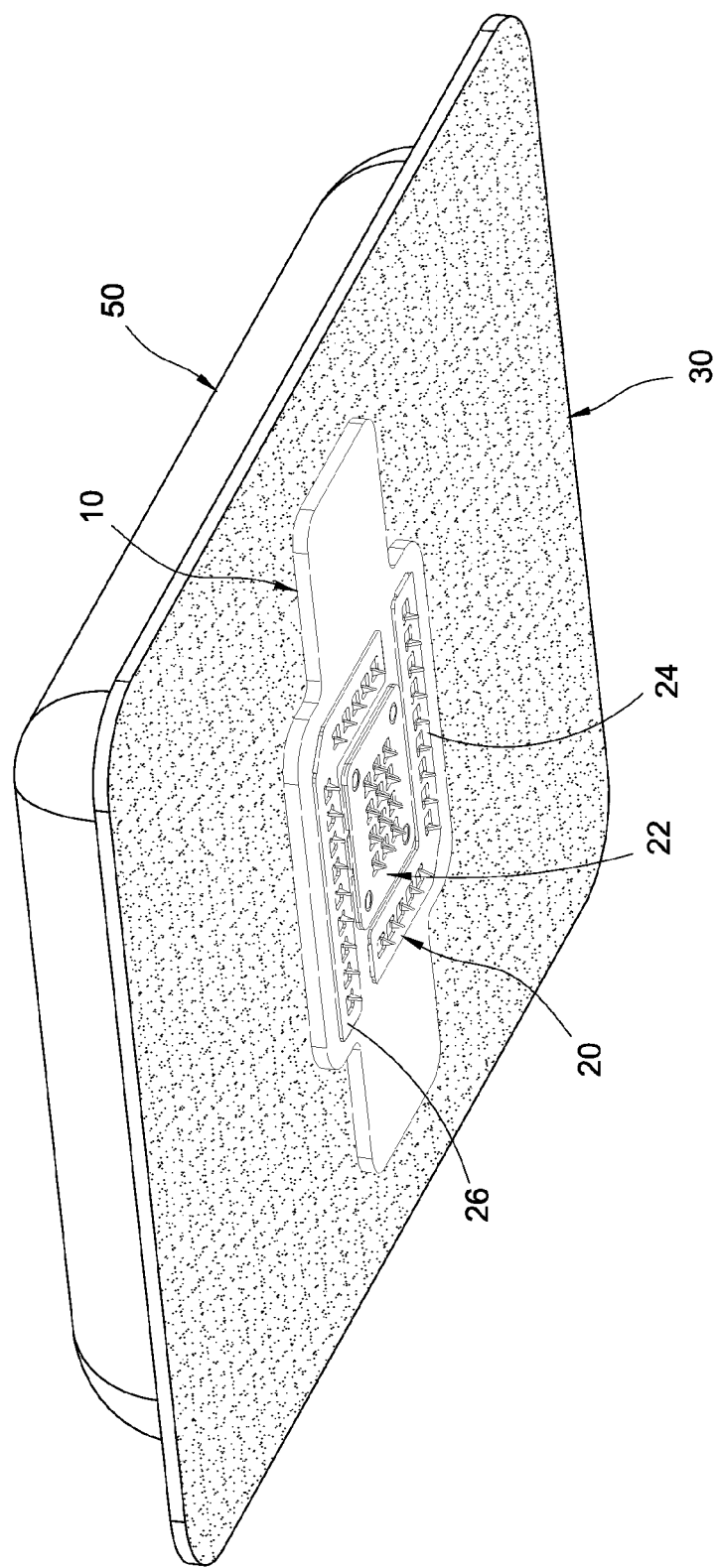
FIG. 8 shows a perspective of an assembled transdermal microneedle array patch according to an embodiment of the present invention.
Figure 9:
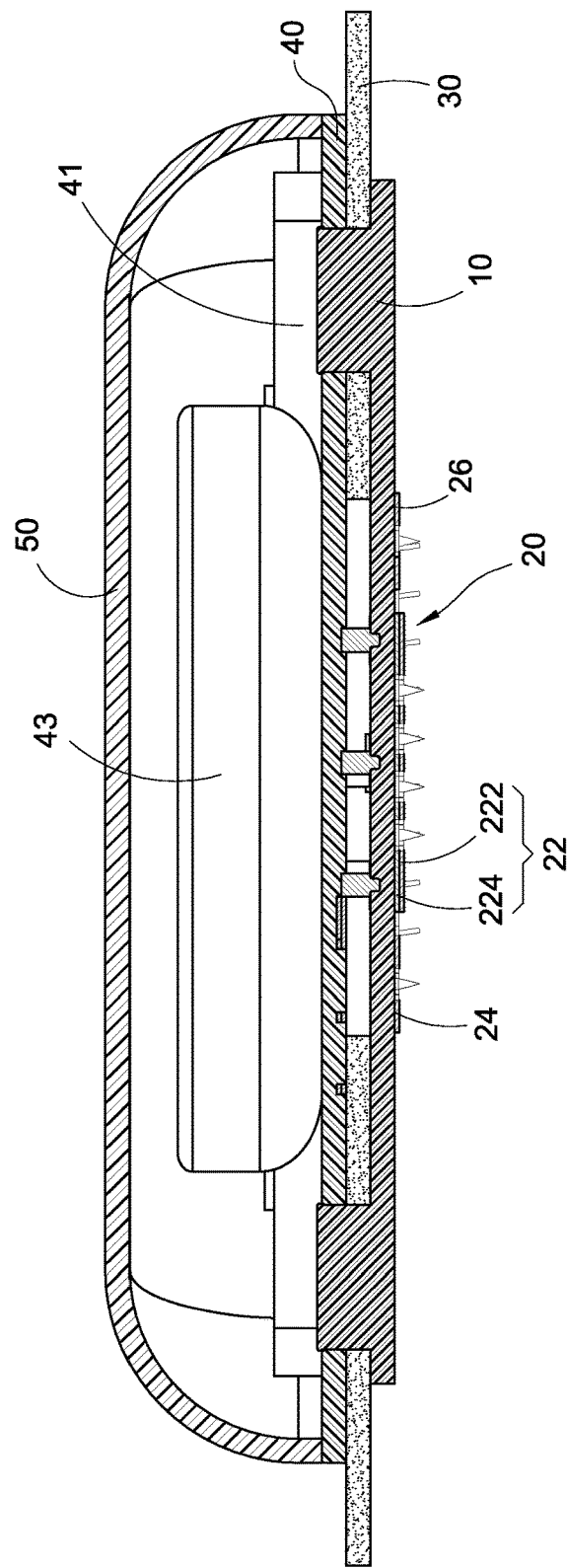
FIG. 9 shows a sectional of an assembled transdermal microneedle array patch according to an embodiment of the present invention.

FIG. 8 shows a perspective of an assembled transdermal microneedle array patch according to an embodiment of the present invention. FIG. 9 shows a sectional of an assembled transdermal microneedle array patch according to an embodiment of the present invention. In this shown embodiment, the first microneedle set 22 comprises a first sheet 222 and a second sheet 224 stacked with each other. The first sheet 222 and the second sheet 224 can be assembled by punching peripherals thereof. The second microneedle set 24 comprises only a first sheet 242 and the third microneedle set 26 comprises only a first sheet 262. The transdermal microneedle array patch of the present invention uses the flexible pad 30 to have tight fit with the user's muscle during operation thereof.

The first microneedle set 22 of the working electrode of the transdermal microneedle array patch according to the invention may be subjected to surface modification, in view of the target molecule to be sensed. The target molecule may be a biological molecule, such as glucose, cortisol or fatty acids. Also, the target molecule may be a pharmaceutical molecule, such as antibiotics. The transdermal microneedle array patch of the present invention may be used for pharmaceutical monitoring during the administration of a medication for a chronic disease or a specific pharmaceutical. Personalized medication of a specific dosage or frequency of administration can be provided based on the individual metabolism of the pharmaceutical.

For specificity, the first microneedle set 22 may be subjected to surface modification, in view of the target molecule to be sensed. Specifically, a molecule selected from the group consisting of an antibody, an aptamer, a single-chain variable fragment (ScFv), a carbohydrate, and a combination thereof, may be coated on the surface of the microneedles. In one embodiment of the present invention, the first microneedle set 22 of the working electrode is modified with glucose oxidase (GOx) for sensing (blood) glucose. For coupling of an antibody or an aptamer, self-assembled monolayer (SAM) may be applied to the microneedle deposited with gold, before adding the antibody or the aptamer. Next, in order to ensure the specificity, a blocking molecule is applied to the position that the antibody or the aptamer fails to be coupled on SAM. To increase sensitivity, carbon nanotubes may be further mixed into the gold layer. Below the various methods for manufacturing modified electrodes are described.

The method for manufacturing streptavidin-modified electrode includes steps as below. The working electrode deposited with a gold layer was treated with 200 mM of 3,3-dithiodipropionic acid for 30 min to form a self-assembled monolayer (SAM), and then washed thoroughly with distilled water. The activation of carboxylic groups were performed on the electrode after incubation with 100 mM of N-(3-dimethylaminopropyl)-N-ethylcarbodiimide (EDC) and 1 mM N-hydroxysuccinimide (NHS) for an hour. Afterward, the electrode was incubated overnight with 1 mg/ml streptavidin in PBS buffer (pH 7.5). The free carboxyl groups on the electrode were blocked by incubation with 100 mM of ethanolamine for 20 min. Finally, 10 nM of biotinylated DNA aptamer was incubated on streptavidin coated electrode for 40 min, and washed thoroughly with distilled water.

Take tetracycline sensing as an example. Tetracycline is an antibiotic commonly used for treating organ inflammation of a patient. For tracing the changes in concentration of tetracycline over time in a patient's body, a transdermal microneedle array patch coupling a biotinylated ssDNA aptamer on a surface of the microneedle of streptavidin-modified electrode is suitable to measure the concentration of tetracycline, wherein the biotinylated ssDNA aptamer has specificity to tetracycline. Therefore, the transdermal microneedle array patch of the present invention may be used for pharmaceutical monitoring during the administration of a medication for a chronic disease or a specific pharmaceutical. Personalized medication of a specific dosage or frequency of administration can be provided based on the individual metabolism of the pharmaceutical.

To increase sensitivity, carbon nanotubes may be further mixed into the gold layer. The method for manufacturing multiwalled carbon nanotube (MWCNT) chemically modified electrode includes steps as below. Carboxylic derivative of CNTs was obtained from commercial available MWCNTs by refluxing in 4M $HNO_3$. The thus obtained oxidized MWCNTs (20 mg) were refluxed in $SOCl_2$ (10 mL) for 12 h. The resulting mixture was decanted, and excess $SOCl_2$ was removed in vacuo. A solution of mercaptoethanol (2 mL, 30 mmol) and of triethylamine (1 mL, 7 mmol) in $CH_2Cl_2$ (10 mL) was added, and the mixture was refluxed for 24 h. The suspension was centrifuged and the solid repeatedly washed with methanol to give derivatized MWCNTs. The MWCNTs-CME was prepared by dipping the cleaned gold electrode in a sonicated suspension of 3 mg of derivatized nanotubes in 1 mL of DMSO for 48 h. Finally, 10 nM of biotinylated DNA aptamer was incubated on streptavidin coated electrode for 40 min, and washed thoroughly with distilled water.

The method for manufacturing single-walled carbon nanotube (SWCNT) chemically modified electrode includes steps as below. Carboxylic derivative of CNTs was obtained from commercial available SWCNTs by refluxing in 4M $HNO_3$. A cystamine monolayer was assembled on the gold electrode to form a self-assembled monolayer (SAM) and the SWCNTs (reactant 2a) that was dispersed by sonicating 3 mg of the material in 1 mL of DMF were linked to the SAM surface in the presence of the coupling reagent, 1,3-dicyclohexylcarbodiimide (DCC, 3 mg) to obtain a product 2b. Next, mercaptoethanol was coupled to the carboxyl groups at the free edges of the product 2b by using DCC (2 mM mercaptoethanol solution in 1 mL of DMF and 3 mg of DCC) to obtain SWCNT chemically modified electrode. Finally, 10 nM of biotinylated DNA aptamer was incubated on streptavidin coated electrode for 40 min, and washed thoroughly with distilled water.

Figure 10:
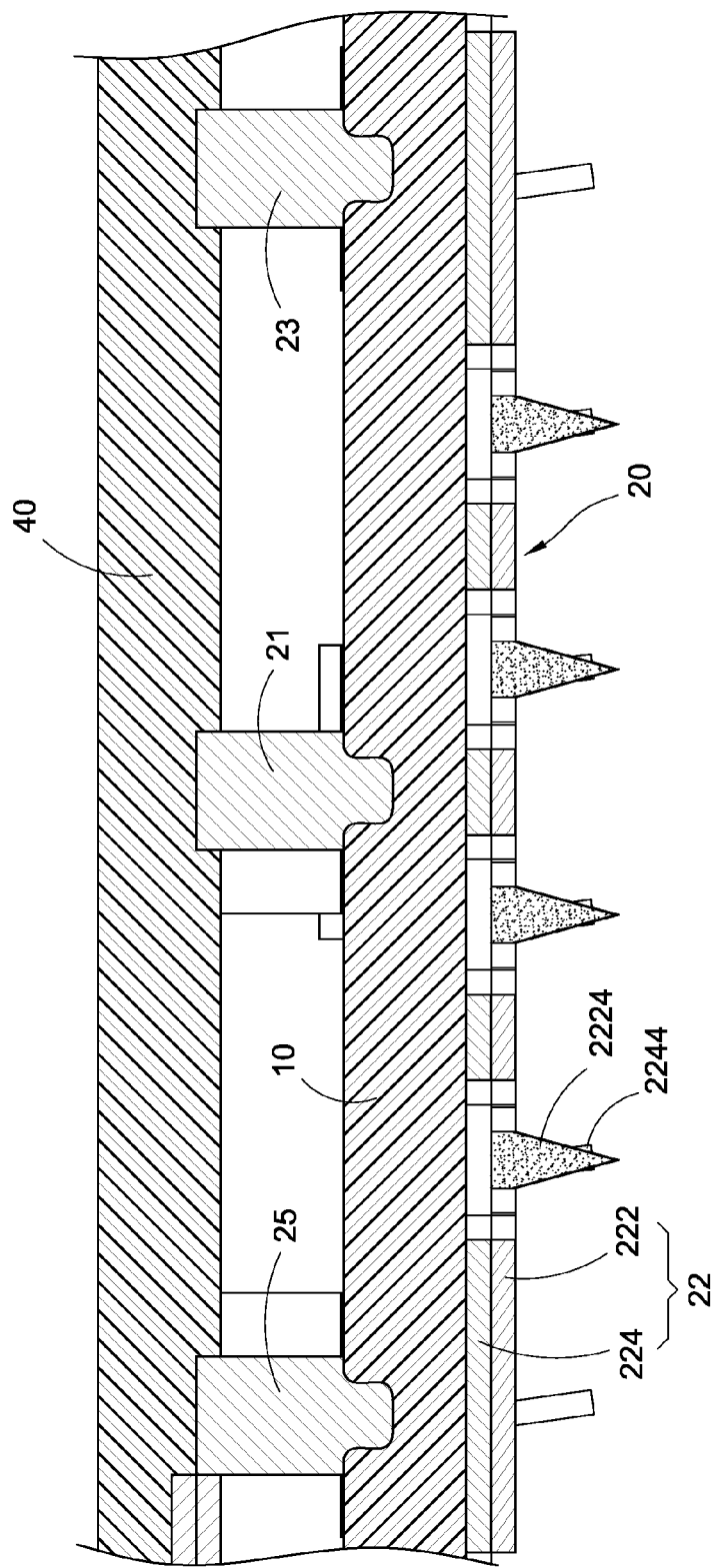
FIG. 10 is a partially sectional view of FIG. 9, where sensing polymer is coated on the barbules.

Next, please refer to FIG. 10. FIG. 10 is a partially sectional view of FIG. 9, where sensing polymer is coated on the barbules. More particularly, the sensing polymer is coated on the inner faces of the barbules, and anti-irritation medicine (medicine preventing skin from irritation) is coated on outer faces of the barbules. In this embodiment, the sensing polymer is a molecule selected from the group consisting of an antibody, an aptamer, a single-chain variable fragment (ScFv), a carbohydrate, glucose oxidase (GOx), hydroxybutyrate dehydrogenase (HBHD), and a combination thereof. The transdermal microneedle array patch having barbules coated with the sensing polymer can sense the concentration data of hypodermal target molecules and determine the current physiological condition of user with the concentration data.

Figure 11:
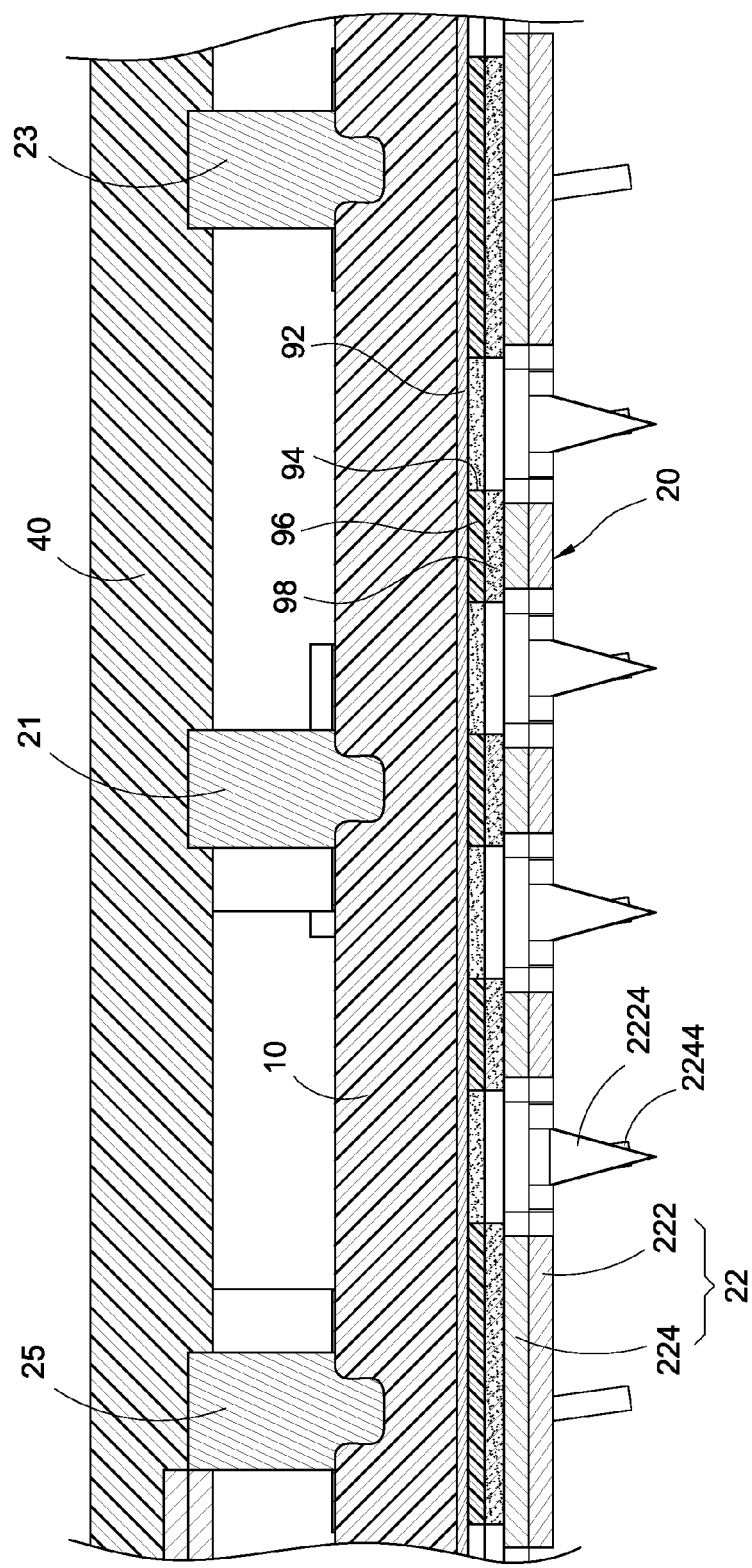
FIG. 11 is a partially sectional view of FIG. 9, where sensing polymer is coated on a test strip.

FIG. 11 is a partially sectional view of FIG. 9, where sensing polymer is coated on a test strip. The embodiment shown in this figure is different with the embodiment of FIG. 10 in that the first microneedle set 22 in this embodiment is used to withdraw interstitial fluid. Therefore, the sensing polymer is coated on a test strip below the first microneedle set 22 instead of coating on the barbules. In this embodiment, the test strip is arranged between the first microneedle set 22 and the substrate 10. The test strip comprises a conductive layer 92 and a plurality of test areas 94 on the conductive layer 92. The test areas 94 are coated with sensing polymer and aligned with the through holes 2222 of the first microneedle set 22. In this embodiment, the test areas 94 are defined by the resin plate 96. Moreover, the first microneedle set 22 is fixed to the test strip by a binding layer 98. In order to prevent the sensing polymer and the anti-irritation medicine from environment pollution, a protection layer such as an epoxy-polyurethane (Epoxy-PU) film is formed on the surface of the sensing polymer and the anti-irritation medicine. Also, since the ammeter electrochemical method is usually less selective, common interferences may present in plasma to interfere the signal. In order to achieve high selectivity for hypodermal target molecule, a semi-permeable membrane or low oxygen permeable membrane is formed on the surface of the electrode, and then a sensing polymer is formed on the semi-permeable membrane or low oxygen permeable membrane.

According to one embodiment of the present invention, a wireless transmission unit (not shown in figures) may further be electrically connected to the signal processing unit 41, and may transmit the sensor signal received from the signal processing unit 41 to a doctor for further review and diagnosis. If the doctor considers that immediate treatment or medication is required, he or she may then send an instruction signal to the user. The wireless transmission unit 41 would receive the instruction signal and the transdermal sensor may provide a signal to remind the user to pay attention to his or her physiological status or to take medication.

Figure 12:
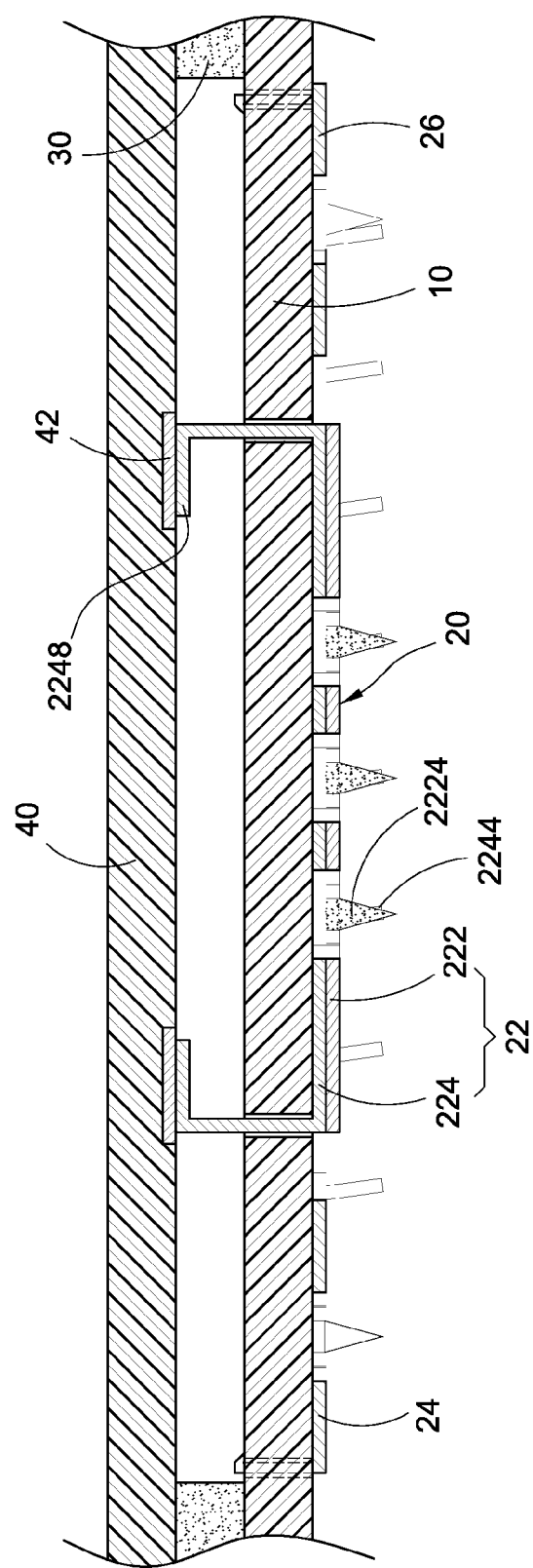
FIG. 12 shows a partially sectional view of an assembled transdermal microneedle array patch according to another embodiment of the present invention.

Next, please refer to FIG. 12. FIG. 12 shows a partially sectional view of an assembled transdermal microneedles continuous monitoring system according to another embodiment of the present invention. In this embodiment, the conductive pin 2248 is bent to electrically connect the contact 42 on the circuit board 40, thus dispensing with the conductive post.

As the skilled person will appreciate, various changes and modifications can be made to the described embodiments. It is intended to include all such variations, modifications and equivalents which fall within the scope of the invention, as defined in the accompanying claims.

What is claimed is:

1. A transdermal microneedle array patch for measuring a concentration of a hypodermal target molecule, comprising:
    a substrate;
    a microneedle unit comprising at least a first microneedle set used as a working electrode and a second microneedle set used as a reference electrode, each of the microneedle sets comprising at least a microneedle, the first microneedle set comprising at least-two sheets, each of the sheets having a through hole defined thereon and a barbule arranged at the peripheral of the through hole, the through hole on one sheet allowing the corresponding barbules of another sheet to pass and the barbules being disposed separately;
    a signal processing unit arranged on the substrate and electrically connecting to the first microneedle set and the second microneedle set; and
    a power supply unit providing working power to the transdermal microneedle array patch.

2. The transdermal microneedle array patch in claim 1, wherein the first microneedle set comprises a first sheet and a second sheet stacked with the first sheet, the first sheet having at least one first through hole defined thereon, and a first barbule at peripheral of the first through hole, the second sheet having at least one second through hole defined thereon and a second barbule at peripheral of the second through hole, wherein the second barbule penetrates the first through hole to juxtapose the first barbule at corresponding location.

3. The transdermal microneedle array patch in claim 2, wherein each of the barbule of the first microneedle set comprises a tip and a base, wherein tips of the barbules are not at the same altitudes after the sheets are stacked and the through hole of one sheet are penetrated by the barbules of other sheets.

4. The transdermal microneedle array patch in claim 2, wherein each of the barbule of the first microneedle set comprises a tip and a base, wherein the tips of the barbules are at the same altitudes after the sheets are stacked and the through hole of one sheet are penetrated by the barbules of other sheets.

5. The transdermal microneedle array patch in claim 1, wherein the first microneedle set comprises a first sheet, a second sheet and a third sheet stacked with each other, the first sheet having at least one first through hole defined thereon, and a first barbule at peripheral of the first through hole, the second sheet having at least one second through hole defined thereon and a second barbule at peripheral of the second through hole, the third sheet having at least one third through hole defined thereon and a third barbule at peripheral of the third through hole, wherein the second barbule and the third barbule penetrate the first through hole to juxtapose the first barbule, and tips of the barbules are in triangular arrangement.

6. The transdermal microneedle array patch in claim 5, wherein each of the barbule of the first microneedle set comprises a tip and a base, wherein tips of the barbules are not at the same altitudes after the sheets are stacked and the through hole of one sheet are penetrated by the barbules of other sheets.

7. The transdermal microneedle array patch in claim 5, wherein each of the barbule of the first microneedle set comprises a tip and a base, wherein the tips of the barbules are at the same altitudes after the sheets are stacked and the through hole of one sheet are penetrated by the barbules of other sheets.

8. The transdermal microneedle array patch in claim 1, wherein the first microneedle set comprises a first sheet, a second sheet, a third sheet and a fourth sheet stacked with each other, the first sheet having at least one first through hole defined thereon, and a first barbule at peripheral of the first through hole, the second sheet having at least one second through hole defined thereon and a second barbule at peripheral of the second through hole, the third sheet having at least one third through hole defined thereon and a third barbule at peripheral of the third through hole, the fourth sheet having at least one fourth through hole defined thereon and a fourth barbule at peripheral of the fourth through hole, wherein the second barbule, the third barbule and the fourth barbule penetrate the first through hole to juxtapose the first barbule, and tips of the barbules are in rectangular arrangement.

9. The transdermal microneedle array patch in claim 8, wherein each of the barbule of the first microneedle set comprises a tip and a base, wherein tips of the barbules are not at the same altitudes after the sheets are stacked and the through hole of one sheet are penetrated by the barbules of other sheets.

10. The transdermal microneedle array patch in claim 8, wherein each of the barbule of the first microneedle set comprises a tip and a base, wherein the tips of the barbules are at the same altitudes after the sheets are stacked and the through hole of one sheet are penetrated by the barbules of other sheets.

11. The transdermal microneedle array patch in claim 1, wherein each of the barbule of the first microneedle set comprises a tip and a base, wherein tips of the barbules are not at the same altitudes after the sheets are stacked and the through hole of one sheet are penetrated by the barbules of other sheets.

12. The transdermal microneedle array patch in claim 1, wherein each of the barbule of the first microneedle set comprises a tip and a base, wherein the tips of the barbules are at the same altitudes after the sheets are stacked and the through hole of one sheet are penetrated by the barbules of other sheets.

13. The transdermal microneedle array patch in claim 1, wherein each the barbules has sensing polymer coated on inner surface thereof.

14. The transdermal microneedle array patch in claim 13, wherein the sensing polymer is a molecule selected from the group consisting of an antibody, an aptamer, a single-chain variable fragment (ScFv), a carbohydrate, and a combination thereof.

15. The transdermal microneedle array patch in claim 1, further comprising a test strip arranged between the first microneedle set and the substrate, the test strip comprises a conductive layer and a plurality of test areas on the conductive layer, the test areas are coated with a sensing polymer and aligned with the through holes of the first microneedle set.

16. The transdermal microneedle array patch in claim 15, wherein the sensing polymer is a molecule selected from the group consisting of an antibody, an aptamer, a single-chain variable fragment (ScFv), a carbohydrate, and a combination thereof.

17. The transdermal microneedle array patch in claim 1, wherein the material of the barbules is selected from the group consisting of stainless steel, nickel, nickel alloy, titanium, titanium alloy, carbon nanotube, and silicon, the surface of the barbules is coated with biologically compatible metal.

18. The transdermal microneedle array patch in claim 1, wherein the material of the barbules is resin, and the surface of the barbules is coated with biologically compatible metal.

19. A method for manufacturing transdermal microneedle array patch, comprising steps:
providing a substrate and a microneedle unit in claim 1;
coating the surface of the barbules of the first microneedle set of the microneedle unit with a biologically compatible metal layer;
forming a self-assembled monolayer on the biologically compatible metal layer;
coupling an antibody or an aptamer to the self-assembled monolayer; and
applying a blocking molecule to a position that the antibody or the aptamer fails to be coupled on the self-assembled monolayer.

20. The method for manufacturing transdermal microneedle array patch in claim 19, further comprising carbon nanotubes mixed into the biologically compatible metal layer.

* * * * *